United States Patent
Stridde et al.

(10) Patent No.: US 6,420,311 B1
(45) Date of Patent: Jul. 16, 2002

(54) POLYETHER DIAMINE—BASED SURFACTANT ADJUVANTS AND COMPOSITIONS THEREOF

(75) Inventors: Howard Meyer Stridde; Samir S. Ashrawi, both of Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/641,228

(22) Filed: Aug. 17, 2000

Related U.S. Application Data

(60) Provisional application No. 60/149,573, filed on Aug. 18, 1999, and provisional application No. 60/149,541, filed on Aug. 18, 1999.

(51) Int. Cl.$^7$ .......................... A01N 3/02; A01N 57/00
(52) U.S. Cl. ...................... 504/116; 504/127; 504/206
(58) Field of Search ................................. 504/116, 127, 504/206

(56) References Cited

U.S. PATENT DOCUMENTS

| | | | |
|---|---|---|---|
| 3,309,182 A | 3/1967 | Crowley et al. | 44/433 |
| 3,639,262 A | 2/1972 | Milligan | 252/355 |
| 5,118,444 A | 6/1992 | Nguyen | 252/390 |
| 5,213,585 A | 5/1993 | Oppenlaender et al. | 44/433 |
| 5,668,085 A | 9/1997 | Forbes et al. | 504/206 |
| 5,683,958 A | 11/1997 | Berger et al. | 504/116 |
| 5,798,310 A | 8/1998 | Toussaint et al. | 504/206 |
| 5,902,772 A | 5/1999 | Magin et al. | 504/206 |

FOREIGN PATENT DOCUMENTS

| | | | |
|---|---|---|---|
| EP | 472 310 | | 2/1992 |
| EP | 489 322 | | 6/1992 |
| EP | 862857 | * | 3/1998 |
| EP | 862 857 | | 9/1998 |
| GB | 2 233 229 | | 1/1991 |
| WO | WO97/05779 | | 2/1997 |
| WO | WO98/24313 | | 6/1998 |
| WO | 9824313 | * | 6/1998 |

OTHER PUBLICATIONS

Huntsman Technical Bulletin Reports, CAS 9046 10 0 D230, D400; CAS 929 59 9.*

International Search Report for PCT application No. PCT/US 00/22542, Filed: Aug. 17, 2000, Applicant: Huntsman Petrochemical Corporation; Date of Completion of International Search Report: Nov. 24, 2000.

Publication: Wyrill, J.B., III, et al.: "Glyphosate Toxicity to Common Milkweed and Hemp Dogbane as Influenced by Surfactants" Weed Science, 1977, 25:275–287.

Technical Bulletins—Huntsman Corporation: #1022–59; "Jeffamine D–230 Polyoxypropylenediamine" 1988 (2 pages) #1100–1096; "XTJ–502 Poly(osyethylene)diamine" 1996 (2 pages) #1021–698; "Jeffamine D–400 Polyoxypropylenediamine" 1998 (2 pages) #1011–1194; "Jeffamine EDR–148 Triethyleneglycoldiamine" 1994 (6 pages).

"Dry Pesticide Formulations—Pesticides and Their Application" Website://agguide.agronomy.psu.edu/sect1 (6 pages).

Quick Glossary for Weed Control Website://www.ewe–chemical.com/glossary (3 pages).

"EXTOXNET" Pesticide Information Profile "Glyphosate" Website: //128.84.37.85/profiles/extox (4 pages).

"Surfactants/wetting agents Non–ionic Surfactants" Website: //scarab.msu.montana.edu (7 pages).

"The Use of Soybean Oil as a Crop Oil for the Application of Herbicides" Slife, F.W. et al., Website://stratsoy.ag.uiuc.edu (2 pages).

"Herbicide Additives" Harzler, R.G., et al., Website: www.p-me.iastate.edu/PAT.pcic/additives (3 pages).

"ChemACX.com" American Radiolabeled Chemicals, Inc. Website:www.chemacx.com (17 pages).

"Phosphorus Pentoxide" Website: //www.chemfinder.com/cgi–win (2 pages).

"ABCR—Data Sheet" Website: //www.c–tronic.de/cgi–bin (1 page).

"Diphosphorus Pentoxide" NIST Chemistry WebBook; Website: //webbook.nist.gov ( 3 pages).

* cited by examiner

*Primary Examiner*—Alton Pryor
(74) *Attorney, Agent, or Firm*—Russell R. Stolle; Nicole Peffer; Christopher J. Whewell

(57) ABSTRACT

Surfactants that are expected to further improve the bioefficacy of herbicides. The surfactants comprise esterified alkoxylated polyether diamines, alkoxylated polyether diamines, and mixtures thereof. The present invention also provides for herbicide compositions that contain the surfactants of the present invention. The herbicide compositions comprise a herbicidal active ingredient, a surfactant of the present invention, and optionally, one or more formulation aids. The present invention additionally provides for a method of controlling unwanted weeds or vegetation using the herbicide compositions of the present invention.

20 Claims, No Drawings

POLYETHER DIAMINE— BASED SURFACTANT ADJUVANTS AND COMPOSITIONS THEREOF

CROSS REFERENCE TO RELATED APPLICATIONS

This application claims the benefit of U.S. Provisional Application Nos. 60/149,573 and 60/149,541, both filed on Aug. 18, 1999.

TECHNICAL FIELD

This invention relates to surfactants, and, more particularly, to surfactants that enhance the bioefficacy of herbicides, and to herbicide compositions comprising such surfactants.

BACKGROUND OF THE INVENTION

Herbicide compositions are often characterized according to the identity of the active ingredient, and by the mode by which the active ingredient causes vegetation necrosis. Regardless of the active ingredient, most herbicides cause vegetation necrosis by interfering with one or more vital biological processes essential to the vegetation's survival. Yet, before the active ingredient of a herbicide can interfere with such biological processes, the active ingredient must somehow be absorbed into the vegetation. Unfortunately, this absorption is often hindered by the chemical nature of the active ingredient.

Accordingly, in addition to active ingredients, most herbicide compositions also comprise other components, commonly termed adjuvants, that enhance the performance and absorption of the active ingredient. One class of adjuvants that is frequently used is surfactants. Surfactants are useful in herbicide compositions because they tend to both enhance the absorbing properties of the active ingredient, as well as facilitate application of the herbicide.

The literature discloses various classes of surfactants, including alkoxylated diamines. However, the literature appears to lack any reference to the use of alkoxylated polyether diamines or esterified alkoxylated polyether diamines as suitable herbicide adjuvants. It is expected that both alkoxylated polyether diamines and esterified alkoxylated polyether diamines will function to improve the bioefficacy of herbicide compositions containing such surfactants. Accordingly, the present invention is directed toward surfactant adjuvants that include alkoxylated polyether diamines, esterified alkoxylated polyether diamines, and mixtures thereof, herbicide compositions comprising such surfactant adjuvants, and a method of controlling unwanted vegetation using such herbicide compositions.

SUMMARY OF THE INVENTION

The present invention provides for surfactants that are expected to further improve the bioefficacy of herbicides. The surfactants comprise alkoxylated polyether diamines (I), esterified alkoxylated polyether diamines (IIa) or (IIb), or mixtures thereof, with the following general structure:

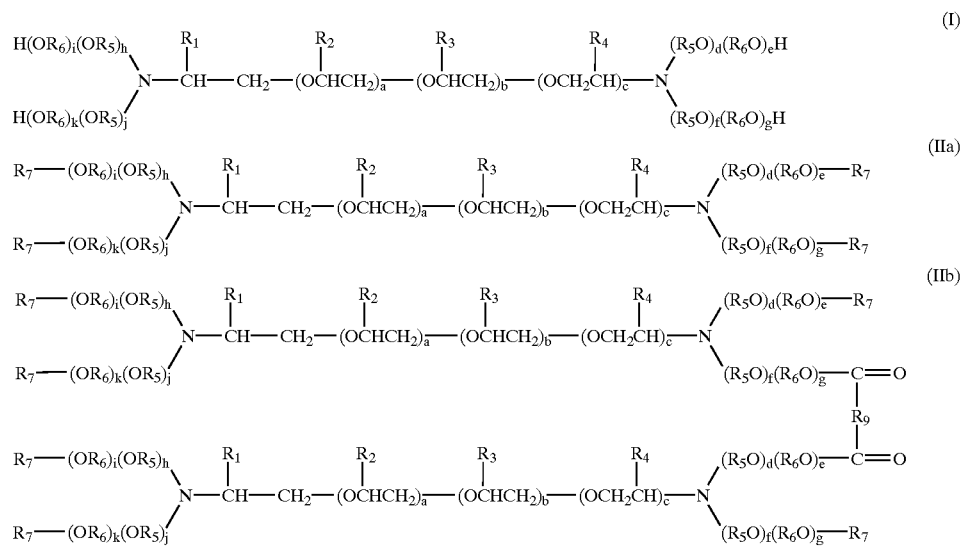

where $R_1$, $R_2$, $R_3$, and $R_4$ are each independently hydrogen, $CH_3$, or $CH_2CH_3$; a, b, and c each vary from zero to about forty; $R_5$ and $R_6$ are each independently a straight or branched chain alkenyl group with from about two to about six carbon atoms; d, e, f, g, h, i, j, and k each vary from zero to about twenty-two; each $R_7$ is independently either a hydrogen or has the following general structure:

where each $R_8$ is independently a linear or branched alkyl or alkenyl with less than about twenty-two carbon atoms; and, $R_9$ is an alkyl or alkenyl with less than about twenty-two carbon atoms.

The present invention also provides for herbicide compositions that contain a surfactant of the present invention. The herbicide compositions comprise a herbicidal active ingredient, a surfactant of the present invention, and optionally, one or more formulation aids. The herbicide compositions of the present invention are expected to have a reduced tendency to cause eye and skin irritation.

The present invention additionally provides for a method of controlling unwanted weeds or vegetation using the herbicide compositions of the present invention.

DETAILED DESCRIPTION OF THE PREFERRED EMBODIMENT

The present invention relates to surfactants that are expected to enhance the bioefficacy of herbicides, herbicide compositions comprising such surfactants, and a method of controlling unwanted weeds or vegetation using the herbicide compositions of the present invention. The surfactants of the present invention are expected to enhance the bioefficacy of herbicides because they have twice the amine content as traditional herbicide surfactants (i.e. tallowamine ethoxylates). This increased amine content will likely enhance the ability of the herbicide to penetrate the tissue of the vegetation, thereby increasing the bioefficacy of the herbicide. In addition, the surfactants of the present invention are expected to have improved handling characteristics, including a lower volatility, due to the polyether "interior" structure of the surfactants. Further, when added to glyphosate solutions, the surfactants of the present invention produce cloud points at or above about 65° C., the commercial standard for glyphosate herbicide solutions.

The surfactants of the present invention may be used in conjunction with any number of herbicidal active ingredients, including, but not limited to, various salts of glyphosate and gluphosinate. However, the use of the surfactants of the present invention with glyphosate is of particular interest because glyphosate is probably the most widely used herbicide.

Glyphosate, or N-phosphonomethylglycine, is a broad-spectrum herbicide that is useful on essentially all annual and perennial plants, including, grasses, broad-leaved weeds, and woody plants. Glyphosate promotes plant necrosis by inhibiting aromatic amino acid biosynthesis. By inhibiting aromatic amino acid synthesis, and thereby protein synthesis, glyphosate initially suppresses plant growth, which is soon followed by plant necrosis.

In its free acid form, glyphosate has a low water solubility. As such, water-based glyphosate compositions typically contain a water soluble salt of glyphosate, such as the isopropylamine salt. For example, many commercially available herbicide compositions contain the water soluble mono-isopropylamine salt of glyphosate. Glyphosate, and various water soluble derivatives of glyphosate are available from numerous manufactures.

The surfactants of the present invention may be prepared by reacting a polyether diamine with one or more lower molecular weight alkylene oxides, at a temperature from about 100° C. to about 110° C., at a pressure of about 60 psig, and in the presence of a suitable alkaline catalyst. The polyether diamines may be alkoxylated to varying degrees. Preferably, the resulting polyether diamines have an alkylene oxide content less than about 90 percent.

The polyether diamine used to make the alkoxylated polyether diamine surfactants of the present invention should have the following general structure:

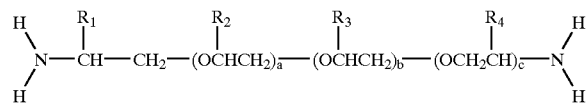

where $R_1$, $R_2$, $R_3$, and $R_4$ are each independently hydrogen, $CH_3$, or $CH_2CH_3$; and a, b, and c each vary from zero to about forty. Preferably, the polyether diamine comprises a JEFFAMINE® diamine (commercially available from the Huntsman Corporation, Houston, Tex.).

The lower molecular weight alkylene oxide may comprise one or more alkylene oxides with less than about six carbon atoms. Preferably, the alkylene oxide comprises ethylene oxide, propylene oxide, butylene oxide, or mixtures thereof.

Any suitable alkoxylation catalyst may be used in the alkoxylation process. Preferably, the catalysts comprises a 45% aqueous solution of potassium hydroxide.

The resulting alkoxylated polyether diamine surfactants of the present invention have the following general structure:

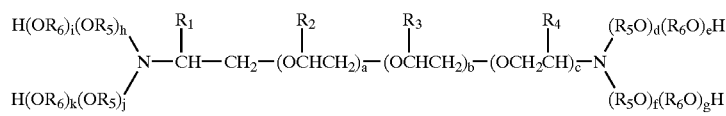

where $R_1$, $R_2$, $R_3$, and $R_4$ are each independently hydrogen, $CH_3$, or $CH_2CH_3$; a, b, and c each vary from zero to about forty; $R_5$ and $R_6$ are each independently a straight or branched chain alkenyl group with from about two to about six carbon atoms; and d, e, f, g, h, i, j, and k each vary from zero to about twenty-two.

After preparation, the resulting alkoxylated polyether diamine surfactants of the present invention may then be blended with one or more formulation aids before being combined with a herbicide. Such formulation aids may include neutralizing agents, water, anti-freeze agents, or mixtures thereof. The neutralizing agents may include, but are not limited to, hydrochloric acid or sulfuric acid, carboxylic acids with less than about twenty carbon atoms, sulfonic acids, acid sulfates, acid phosphate esters, and/or acid carboxylates. A sufficient amount of a neutralizing agent should be added to the surfactant to neutralize any residual basicity (i.e to achieve a pH of about 7.0). The anti-freeze agents may include, but are not limited to ethylene glycol, diethylene glycol, propylene glycol, and polyethylene glycols.

The relative amount of formulation aids that should be blended with the alkoxylated polyether diamine surfactants of the present invention will depend on a variety of factors, including the nature of the herbicide to be blended with the surfactant solution, the proposed mode of application of the final herbicide formulation, the nature of the vegetation to be treated, etc.

Alternatively, the alkoxylated polyether diamines may be esterified by reacting the alkoxylated polyether diamines with one or more carboxylic acids. The esterification reaction should take place at a temperature from about 190° C. to about 210° C., in an esterification vessel, with agitation, under nitrogen, and in the presence of an acid catalyst. The esterification reaction should proceed until all the water produced by the esterification reaction has been collected.

The carboxylic acid may include, but is not limited to, alkyl, alkylene, aryl, alkylaryl monocarboxylic acids or dicarboxylic acids with less than about twenty-two carbon atoms, carboxylic acids based on non-ionic surfactants formed from the reaction of a OH-containing hydrophobe and various alkylene oxides (ether carboxylates), or mixtures thereof. Preferably, the carboxylic acid comprises a tall oil fatty acid.

The catalyst may comprise any suitable esterification catalyst. Preferably, the acid catalyst comprises p-toluenesulfonic acid.

If the alkoxylated polyether diamines are esterified with a monocarboxylic acid(s), the resulting esterified alkoxylated polyether diamines have the following general structure:

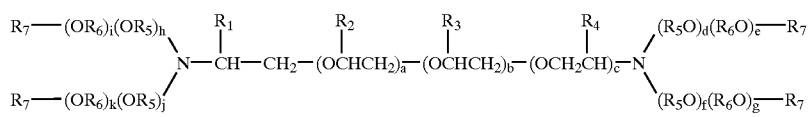

where $R_1$, $R_2$, $R_3$, and $R_4$ are each independently hydrogen, $CH_3$, or $CH_2CH_3$; a, b, and c each vary from zero to about forty; $R_5$ and $R_6$ are each independently a straight or branched chain alkenyl group with from about two to about six carbon atoms; d, e, f, g, h, i, j, and k each vary from zero to about twenty-two; and each $R_7$ is independently either a hydrogen or has the following general structure:

where each $R_8$ is independently a linear or branched alkyl or alkenyl with less than about twenty-two carbon atoms.

If the alkoxylated polyether diamines are esterified with a dicarboxylic acid, or a dicarboxylic acid and a monocarboxylic acid(s), the resulting esterified alkoxylated polyether diamines have the following general structure:

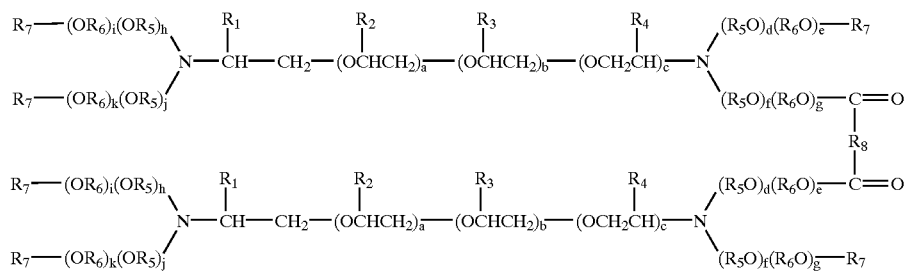

where $R_1$, $R_2$, $R_3$, and $R_4$ are each independently hydrogen, $CH_3$, or $CH_2CH_3$; a, b, and c each vary from zero to about forty; $R_5$ and $R_6$ are each independently a straight or branched chain alkenyl group with from about two to about six carbon atoms; d, e, f, g, h, i, j, and k each vary from zero to about twenty-two; each $R_7$ is independently either a hydrogen or has the following general structure:

where each $R_8$ is independently a linear or branched alkyl or alkenyl with less than about twenty-two carbon atoms; and, $R_9$ is an alkyl or alkenyl with less than about twenty-two carbon atoms.

The resulting esterified alkoxylated polyether diamine surfactants of the present invention may then be blended with one or more formulation aids before being combined with a herbicide. Such formulation aids may include neutralizing agents, water, anti-freeze agents, or mixtures thereof. The neutralizing agents may include, but are not limited to, hydrochloric acid or sulfuric acid. A sufficient amount of a neutralizing agent should be added to the surfactant to neutralize any residual basicity (i.e to achieve a pH of about 7.0). The anti-freeze agents may include, but are not limited to ethylene glycol, diethylene glycol, propylene glycol, and polyethylene glycols.

The relative amount of formulation aids that should be blended with the esterified alkoxylated polyether diamine surfactants of the present invention will depend on a variety of factors, including the nature of the herbicide to be blended with the surfactant solution, the proposed mode of application of the final herbicide formulation, the nature of the vegetation to be treated, etc.

After preparation, the alkoxylated polyether diamine and esterified alkoxylated polyether diamine surfactant compositions of the present invention, or mixtures thereof, may then be blended with a herbicide. The relative amount of the alkoxylated polyether diamine and/or esterified alkoxylated polyether diamine surfactant compositions of the present invention that should be blended with a herbicide will vary depending on a variety of factors, including the nature of the herbicide, the nature of the vegetation to be treated, the method of application, whether the herbicide is a water-based or a granular formulation, etc. In any case, the resulting herbicide compositions of the present invention should include a herbicidally effective amount of a herbicidal active ingredient, and a sufficient amount of a surfactant composition of the present invention to enhance the effectiveness of the herbicidal active ingredient. The term "herbicidally effective amount" means the amount of herbicide necessary to promote plant necrosis. The term "surfactant composition" means the surfactants of the present invention blended with one or more formulation aids.

The herbicide compositions of the present invention may be prepared as either liquid or solid compositions. Liquid compositions may include solutions ready for immediate application, aqueous concentrates intended to be diluted with water before application, or microencapsulated actives suspended in liquid media. Solid compositions may include, but are not limited to, water dispersible granules, water soluble granules, microencapsulated actives, free-flowing particulate compositions, or granular-based solids that have been compressed into tablets or briquets of any desired size and shape. Optionally, solid compositions may include formulations where the herbicide composition is absorbed onto water soluble or water insoluble inert dry carriers, including, but not limited to, Magnesol® (commercially available from the Dallas Group of America, Inc., Whitehouse, N.J.).

Accordingly, the herbicide compositions of the present invention may be applied to vegetation as either a liquid or solid composition. Liquid herbicide compositions are typically sprayed on the vegetation to be treated, and typically comprise either liquid concentrates or dissolved or dispersed solid compositions. Liquid compositions may also be injected into, or painted on the truck portion of the vegetation to be treated. Solid granular compositions may be spread on or around the vegetation to be treated.

Herbicide compositions comprising the alkoxylated polyether diamine and/or esterified alkoxylated polyether diamine surfactant compositions of the present invention are expected to have a reduced tendency to cause eye irritation. Reduced eye irritation is expected because the pH of the alkoxylated polyether diamine and esterified alkoxylated polyether diamine surfactant compositions of the present invention is about 7.0. Because herbicide formulations are often applied by humans, or in locales with humans or animals, reduced eye irritation is a desirable feature in such formulations.

It is understood that variations may be made in the foregoing with departing from the scope of the invention. For example, although the surfactants of the present invention are primarily discussed as being incorporated into water-based herbicide compositions, it is understood that the surfactants of the present invention may also be incorporated into dry granular herbicide formulations. In addition, although the surfactants of the present invention are primarily discussed as being incorporated into glyphosate solutions, the surfactants of the present invention may be incorporated into any number of other herbicide formulations, including, but not limited to, macro and micro emulsions, suspensions, suspension concentrates, and other liquid and solid formulations known to those skilled in the art, to increase the bioefficacy of such herbicides.

The following examples are illustrative of the present invention, and are not intended to limit the scope of the invention in any way.

Preparation of the Alkoxylated Polyether Diamines

EXAMPLE 1

20 pounds of JEFFAMINE® XTJ-511 were charged to a nitrogen purged reactor. The reactor pressure was then increased to 60 psig, and vented down to 0 three times. The reactor was then purged with nitrogen, at a temperature of about 115° C., until the weight percent of water was reduced to less than 0.05%. The JEFFAMINE® XTJ-511 was then reacted with ethylene oxide to produce a product with varying degrees of ethylene oxide content. The ethoxylation was conducted at a temperature from about 100° C. to about 110° C., at a pressure of about 60 psig, and in the presence of a 45% aqueous potassium hydroxide solution.

Preparation of a Surfactant Solution Containing the Alkoxylated Polyether Diamine

EXAMPLE 2

The alkoxylated polyether diamine produced in Example 1 (with a 10% ethylene oxide content) was then blended to achieve a pH neutral solution, as follows:

| Component | Amount |
|---|---|
| Alkoxylated polyether diamine w/a 10% EO content produced in Example 1 | 73% |
| Concentrated HCl | 20% |
| Water | 7% |

Bioefficacy Testing of Glyphosate Solutions Containing the Alkoxylated Polyether Diamine Surfactants of the Present Invention

EXAMPLE 3

(Prophetic)

The surfactant solution prepared in Example 2 is then blended with a glyphosate solution. Rodeo® is used as the source of glyphosate. (Rodeo® contains 648 g/L of the mono-isopropylamine salt of glyphosate.) The glyphosate solution is then sprayed on a variety of weeds. The weeds are examined approximately twenty-one days after treatment with the glyphosate solution containing a surfactant of the present invention. The weeds appear to be significantly affected by the treatment, and most appear to be dead.

Preparation of the Esterified Alkoxylated Polyether Diamines

EXAMPLE 4

4.7 pounds of JEFFAMINE® XTJ-511 were charged to a nitrogen purged reactor. The reactor pressure was then increased to 60 psig, and vented down to 0 three times. The reactor was then purged with nitrogen, at a temperature of about 115° C., until the weight percent of water was reduced to less than 0.05%. The JEFFAMINE® XTJ-511 was then reacted with ethylene oxide to produce a product with about a 30% ethylene oxide content. The reaction was conducted at a temperature from about 100° C. to about 110° C., at a pressure of about 60 psig, and in the presence of a 45% aqueous potassium hydroxide solution.

850.3 grams of the alkoxylated polyether diamine prepared above and 149.7 grams of a tall oil fatty acid were charged to a three-necked flask. The reaction components were then heated to a temperature from about 190° C. to about 210° C., with agitation, under nitrogen sparge and vacuum. Then, approximately 1 percent of p-toluenesulfonic acid was added, and the esterification reaction was continued until the calculated water of esterification had been collected.

Preparation of a Surfactant Solution Containing the Esterified Alkoxylated Polyether Diamine

EXAMPLE 5

The esterified alkoxylated polyether diamine produced in Example 4 was then blended to achieve a pH neutral solution, as follows:

| Component | Amount |
|---|---|
| Esterified alkoxylated polyether diamine produced in Example 4 | 78.4% |
| Concentrated HCl | 4.6% |
| Water | 17.0% |

Bioefficacy Testing of Glyphosate Solutions Containing the Esterified Alkoxylated Polyether Diamine Surfactants of the Present Invention

EXAMPLE 6

(Prophetic)

The surfactant solution prepared in Example 5 is then blended with a glyphosate solution. Rodeo® is used as the source of glyphosate. (Rodeo® contains 648 g/L of the mono-isopropylamine salt of glyphosate.) The glyphosate solution is then sprayed on a variety of weeds. The weeds are examined approximately twenty-one days after treatment with the glyphosate solution containing a surfactant of the present invention. The weeds appear to be significantly affected by the treatment, and most appear to be dead.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A herbicide composition that comprises:

a. a herbicidally effective amount of a herbicidal active ingredient; and b. a sufficient amount of a surfactant component that enhances the effectiveness of the herbicidal active ingredient, wherein the surfactant component comprises either alkoxylated polyether diamines (I), esterified alkoxylated polyether diamines (IIa) or (IIb), or mixtures thereof, with the following general structure:

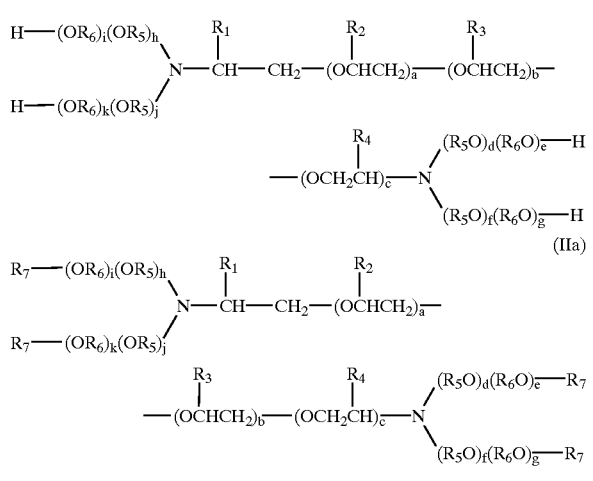

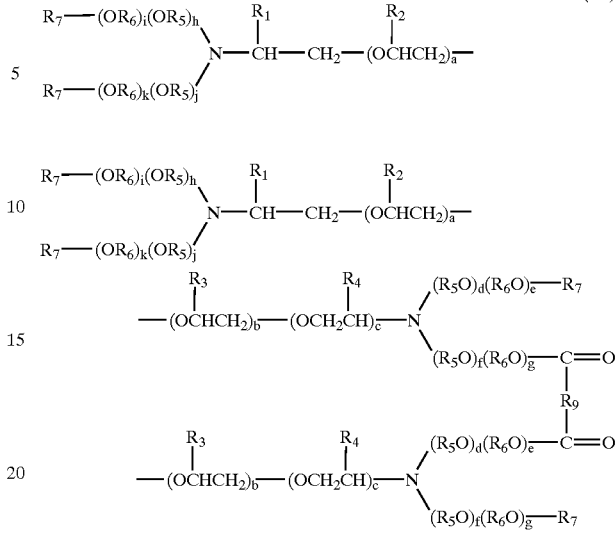

where $R_1$, $R_2$, $R_3$, and $R_4$ are each independently hydrogen, $CH_3$, or $CH_2CH_3$; a, b, and c each vary from zero to about forty, subject to the proviso that at least one of a, b, or c is not zero; $R_5$ and $R_6$ are each independently a straight or branched chain alkenyl group with from about two to about six carbon atoms; d, e, f, g, h, i, j, and k each vary from zero to about twenty-two, subject to the proviso that at least one of d, e, f, g, h, i, j, and k is not zero; each $R_7$ is independently either a hydrogen or has the following general structure:

where each $R_8$ is independently a linear or branched alkyl or alkenyl with less than about twenty-two carbon atoms; and, $R_9$ is a bridging alkyl or alkenyl with less than about twenty-two carbon atoms.

2. The composition of claim 1, wherein the herbicidal active ingredient comprises glyphosate or a salt thereof.

3. The composition of claim 1, wherein $R_5$ and $R_6$ are each independently a straight or branched chain alkenyl group with from about two to about four carbon atoms.

4. The composition of claim 1, wherein the surfactant component further comprises a formulation aid.

5. The composition of claim 4, wherein the formulation aid is selected from the group consisting of neutralizing agents, water, anti-freeze agents, and mixtures thereof.

6. The composition of claim 5, wherein the neutralizing agent is selected from the group consisting of hydrochloric acid, sulfuric acid, carboxylic acids with less than about twenty carbon atoms, sulfonic acids, acid sulfates, acid phosphate esters, and acid carboxylates.

7. A method of killing or controlling weeds or unwanted vegetation comprising the step of applying a herbicidally effective amount of the composition of claim 1 to the foliage or tissue of the weeds or unwanted vegetation.

8. A herbicide composition that comprises:

a. a herbicidally effective amount of glyphosate or a salt thereof; and b. a sufficient amount of a surfactant component that enhances the effectiveness of glyphosate or a salt thereof, wherein the surfactant component comprises either alkoxylated polyether diamines (I), esterified alkoxylated polyether diamines (IIa) or (IIb), or mixtures thereof, with the following general structure:

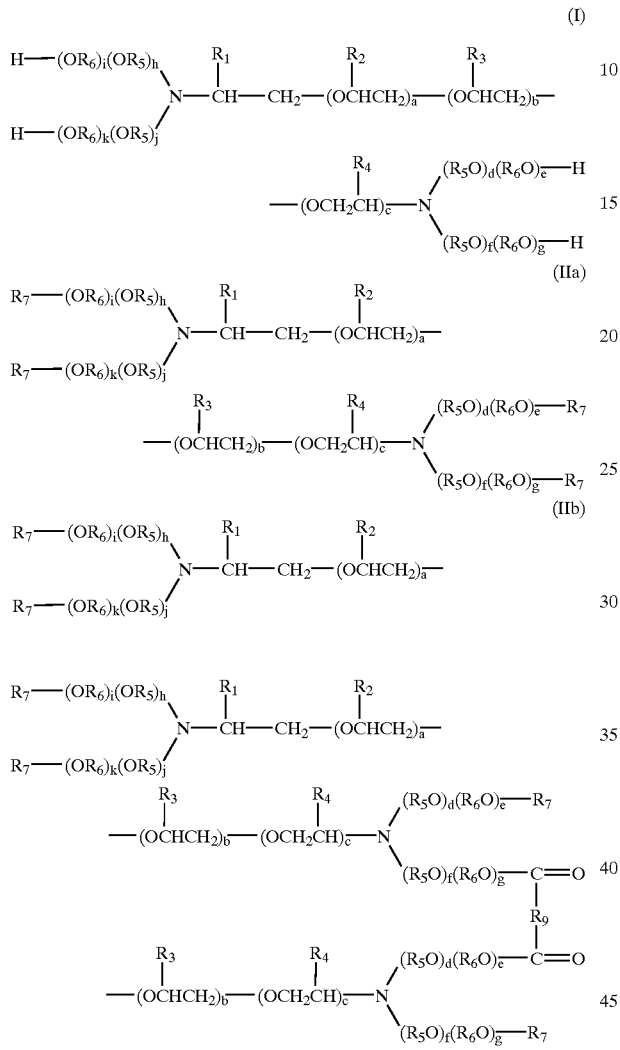

where $R_1$, $R_2$, $R_3$, and $R_4$ are each independently hydrogen, $CH_3$, or $CH_2CH_3$; a, b, and c each vary from zero to about forty, subject to the proviso that at least one of a, b, or c is not zero; $R_5$ and $R_6$ are each independently a straight or branched chain alkenyl group with from about two to about six carbon atoms; d, e, f, g, h, i, j, and k each vary from zero to about twenty-two, subject to the proviso that at least one of d, e, f, g, h, i, j, and k is not zero; each $R_7$ is independently either a hydrogen or has the following general structure:

where each $R_8$ is independently a linear or branched alkyl or alkenyl with less than about twenty-two carbon atoms; and, $R_9$ is a bridging alkyl or alkenyl with less than about twenty-two carbon atoms.

9. The composition of claim 8, wherein $R_5$ and $R_6$ are each independently a straight or branched chain alkenyl group with from about two to about four carbon atoms.

10. The composition of claim 8, wherein the surfactant component further comprises a formulation aid.

11. The composition of claim 10, wherein the formulation aid is selected from the group consisting of neutralizing agents, water, anti-freeze agents, and mixtures thereof.

12. The composition of claim 11, wherein the neutralizing agent is selected from the group consisting of hydrochloric acid, sulfuric acid, carboxylic acids with less than about twenty carbon atoms, sulfonic acids, acid sulfates, acid phosphate esters, and acid carboxylates.

13. A method of killing or controlling weeds or unwanted vegetation comprising the step of applying a herbicidally effective amount of the composition of claim 8 to the foliage or tissue of the weeds or unwanted vegetation.

14. A surfactant for increasing the bioefficacy of a herbicide, wherein the surfactant comprises either alkoxylated polyether diamines (I), esterified alkoxylated polyether diamines (IIa) or (IIb), or mixtures thereof, with the following general structure:

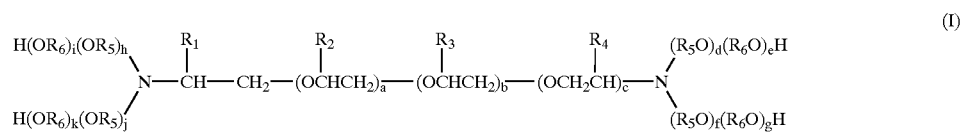

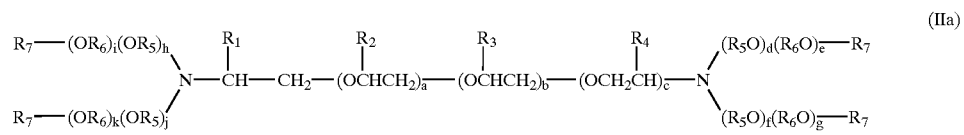

-continued

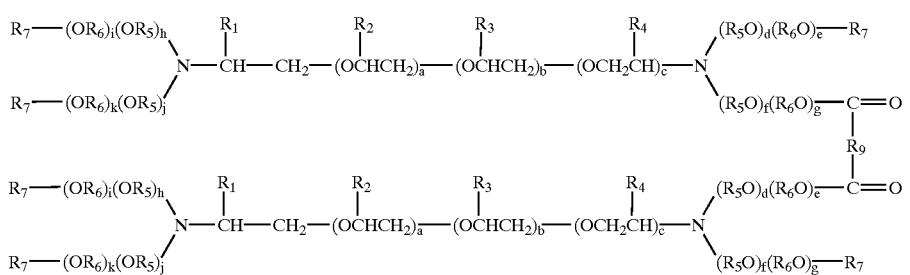

where $R_1$, $R_2$, $R_3$, and $R_4$ are each independently hydrogen, $CH_3$, or $CH_2CH_3$; a, b, and c each vary from zero to about forty, subject to the proviso that at least one of a, b, or c is not zero; $R_5$ and $R_6$ are each independently a straight or branched chain alkenyl group with from about two to about six carbon atoms; d, e, f, g, h, i, j, and k each vary from zero to about twenty-two, subject to the proviso that at least one of d, e, f, g, h, i, j, and k is not zero; each $R_7$ is independently either a hydrogen or has the following general structure:

where each $R_8$ is independently a linear or branched alkyl or alkenyl with less than about twenty-two carbon atoms; and, $R_9$ is a bridging alkyl or alkenyl with less than about twenty-two carbon atoms.

15. The surfactant of claim 14, wherein $R_5$ and $R_6$ are each independently a straight or branched chain alkenyl group with from about two to about four carbon atoms.

16. A surfactant for increasing the bioefficacy of a herbicide that comprises:

a. alkoxylated polyether diamines (I), esterified alkoxylated polyether diamines (IIa) or (IIb), or mixtures thereof, with the following general structure:

where $R_1$, $R_2$, $R_3$, and $R_4$ are each independently hydrogen, $CH_3$, or $CH_2CH_3$; a, b, and c each vary from zero to about forty, subject to the proviso that at least one of a, b, or c is not zero; $R_5$ and $R_6$ are each independently a straight or branched chain alkenyl group with from about two to about six carbon atoms; d, e, f, g, h, i, j, and k each vary from zero to about twenty-two, subject to the proviso that at least one of d, e, f, g, h, i, j, and k is not zero; each $R_7$ is independently either a hydrogen or has the following general structure:

where each $R_8$ is independently a linear or branched alkyl or alkenyl with less than about twenty-two carbon atoms; and, $R_9$ is a bridging alkyl or alkenyl with less than about twenty-two carbon atoms; and b. a formulation aid.

17. The composition of claim 16, wherein $R_5$ and $R_6$ are each independently a straight or branched chain alkenyl group with from about two to about four carbon atoms.

18. The composition of claim 16, wherein the formulation aid is selected from the group consisting of water, neutralizing agents, anti-freeze agents, dyes, thickening agents, anti-foaming agents, UV stabilizers, and mixtures thereof.

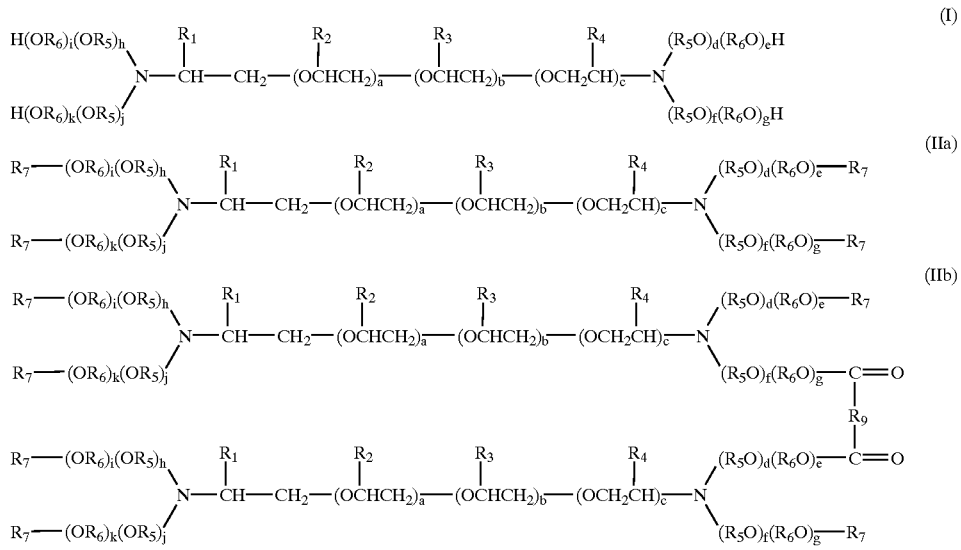

19. The composition of claim 18, wherein the neutralizing agent is selected from the group consisting of hydrochloric acid, sulfuric acid, carboxylic acids with less than about twenty carbon atoms, sulfonic acids, acid sulfates, acid phosphate esters, and acid carboxylates.

20. The composition of claim 16, wherein the composition has a cloud point greater than about 65° C. when mixed with a herbicidal active ingredient.

* * * * *